United States Patent [19]

Baclit et al.

[11] Patent Number: 4,726,074
[45] Date of Patent: Feb. 23, 1988

[54] DETACHABLE VISOR

[76] Inventors: Paul Baclit, 2167 College View Dr., Monterey Park, Calif. 91754; Chi K. Chang, 400 North Serrano Ave., Apt. #210, Los Angeles, Calif. 90004

[21] Appl. No.: 927,431
[22] PCT Filed: Mar. 15, 1985
[86] PCT No.: PCT/US85/00425
 § 371 Date: Oct. 27, 1986
 § 102(e) Date: Oct. 27, 1986
[87] PCT Pub. No.: WO 86/05 368
 PCT Pub. Date: Sep. 25, 1986

[51] Int. Cl.⁴ .......................... A42B 1/24; A61F 9/04
[52] U.S. Cl. ........................................ 2/10; 2/185 R; 2/431; 2/453
[58] Field of Search ............... 2/8, 9, 10, 173, 206, 2/424, 453, 185 R, 191, 431

[56] References Cited

U.S. PATENT DOCUMENTS

| | | | |
|---|---|---|---|
| 1,725,340 | 8/1929 | Castriotis | 2/10 |
| 2,013,636 | 9/1935 | Shoskey et al. | 2/10 |
| 2,449,303 | 9/1948 | Laing | 2/453 |
| 2,519,959 | 8/1950 | Fisher | 2/10 |
| 2,915,756 | 12/1959 | Rex et al. | 2/8 |
| 3,120,002 | 2/1964 | Blumenthal | 2/9 |
| 3,214,767 | 11/1965 | Weber | 2/9 |
| 4,210,972 | 7/1980 | Baclit | 2/10 |

FOREIGN PATENT DOCUMENTS 476306 7/1915 France ........................... 2/10

Primary Examiner—Wm. Carter Reynolds
Attorney, Agent, or Firm—Albert O. Cota

[57] ABSTRACT

A visor for a billed type hat having a holder (20) of similar configuration to the periphery of the bill with a lens (40) distending at right angles downward in front of the bill covering the wearers eyes. A socket (26) within the holder (20) rotatably connected to a link (50) provides vertical movement and a jaw (58) is further rotatably attached to the link (50). The jaw also contains a pair of fingers (64) that springingly separate to grasp the bill of a cap near the crown. The device rotates upward from the cap and, through friction of the rotating members, remains in the elevated position at the wearers option.

4 Claims, 12 Drawing Figures

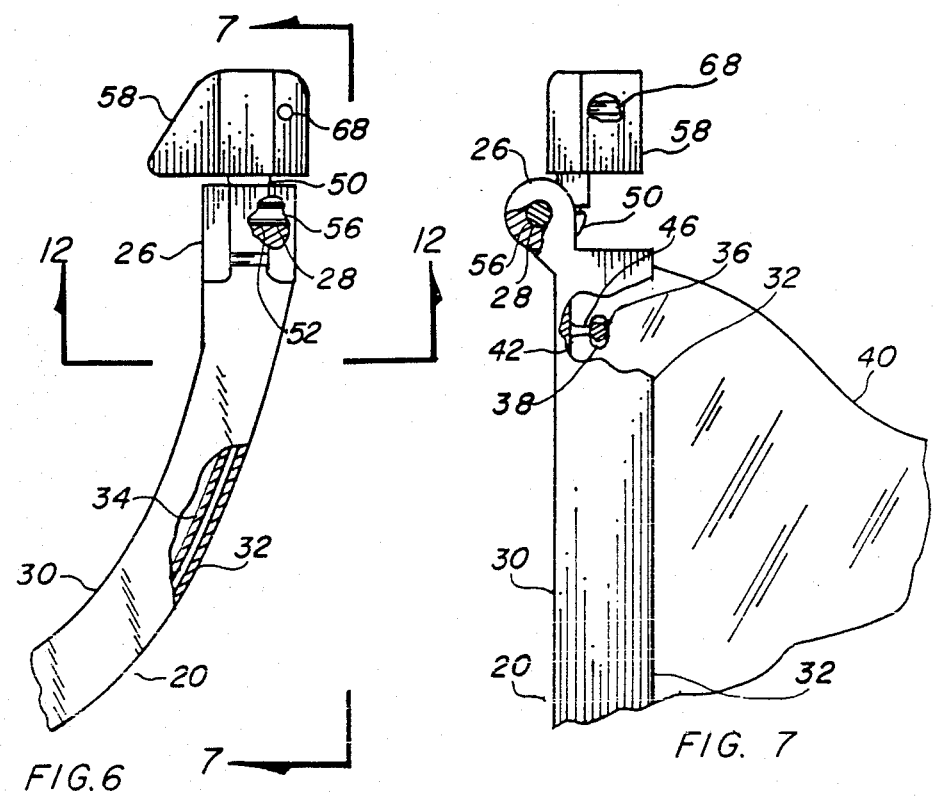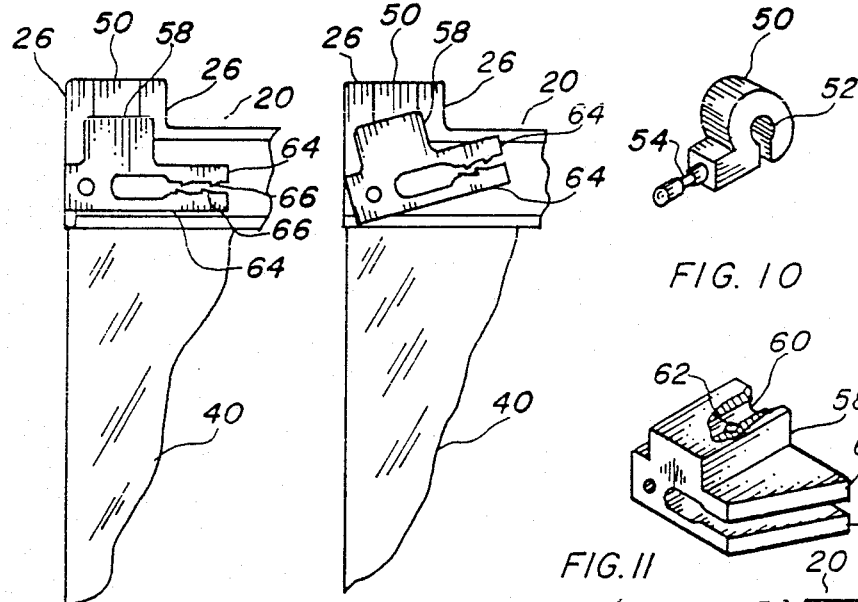

DETACHABLE VISOR

TECHNICAL FIELD

The invention relates to optically protecting eye shields attached to hats in general, and more specifically to a detachable visor mountable upon the bill of a cap rotating upward away from the wearers face when not in use.

BACKGROUND ART

For background purposes and as indicative of the art to which this invention relates attention is directed to a prior U.S. Pat. No. 4,210,972 issued to the instant inventor on July 8, 1980. This patent discloses a detachable visor arrangement that fits on the bill of the cap with a single plane hinge that rotates in a unitary direction. The hinge, as previously taught by the inventor, was comprised of a first and second hinge means as a separate and distinct element, one end attached to the clip and the other to the arcuate rim. Further, the hinge required a pin or round member therebetween with only one rotational plane allowed.

A first, second, and third restraining means was also claimed to allow the visor to be locked into place in the face guarding position, and also the clear or the locked position. A separate protuberance and a receiving cavity were utilized to accomplish this final function.

Further, the face shield was permanently attached to the rim on the outside with a plurality of fasteners, as depicted in FIGS. 1, 3-5, making the shield an integral part of the device.

A single internal tooth was provided on the clip and no allowance was granted in the clip for expansion to slip over the caps bill locking it into place.

DISCLOSURE OF THE INVENTION

The prior art of the applicants, although containing functional capabilities, was found considerably lacking in the relationship of some elements allowing operation in an acceptable manner. As an example, the clips holding the device onto the bill of a cap only hinged upwardly. Inasmuch as most billed caps are slightly concave on the bottom surface, attachment of the visor had a tendency to straighten out the bill and cause a deformation at the end attached to the covering member also causing a torsional load to the rim slightly bowing it at each end. When the assembly was lifted up into the stowed position the reverse action took place.

As some functional refinements were obviously needed and advancement in the art to increase the versatility was desired, it is a primary object of the invention to improve the detachable visor by adding a completely separate hinge element. This swivel link not only hinges vertically, but rotates laterally. With this improvement the invention is adaptable with hats having any configuration of the bill, convex, concave, or flat. Now the shape of the hat is not critical and with the adaptation of a further advanced combination of elements, the visor may be lifted into any angular position and be retained in that station. With this ability any position may be maintained eliminating completely the lock or restraining means taught in the prior invention. Utility is increases as the user may now elevate the visor just sufficiently to see under, for close observation, while still allowing the lens to shade ones eyes. Also, it may be moved flush with the end of the bill on the cap for easy return or completely raised to an out of the way position, being still available when wanted.

An important object of the improvement is to eliminate completely the requirement to remove the visor from the hat and reverse it end for end to lock it into a storage position when not in use. This requirement of prior art was time consuming and created wear on the hat with constant moving of the resiliently deformable clips. Further, the locking mechanism of a protuberance extending into a cavity was delicate and required a physical effort to lock and unlock, also, it was easily broken off with slight abuse.

Another object of the improvement is to make the lens removable from the rim or holder. As it is desirable to have the capability to interchange lenses for color variation, density, and shape with the invention, prior art was lacking in this capacity. The improvement utilizes a pair of downwardly depending legs with a plurality of sleeves pressed into the inside leg with the lens having mating keyhole shaped holes. To interchange the lens, it may be simply pulled downward until it disengages and the replacement forced onto the sleeves making the exchange easy and positive.

Still another object takes advantage of a resilient mounting jaw or clip with a thinned portion near the intermost area allowing the fingers to spread easily to fit a wider variety of bill thicknesses. Also, multiple teeth are introduced to provide an extended gripping surface. This improvement adds considerable versatility and prolongs its useful life.

Yet another object introduces a different shape of the lens, increasing the surface area extending the coverage of ones face by providing a shape that superimposes the cheeks while being cut-away to clear the wearers nose.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 6 is a partial plan view taken along lines 6—6 of FIG. 2.

FIG. 7 is a view taken along lines 7—7 of FIG. 6 with some areas cut-away for clarity.

FIG. 8 is a partial end view taken along lines 8—8 of FIG. 3 with the mounting jaw horizontal.

FIG. 9 is a partial end view taken along lines 9—9 of FIG. 3 with the mounting jaw angularly rotated.

FIG. 10 is a partial isometric view of one of the swivel links completely removed from the invention for clarity.

FIG. 11 is a partial isometric view of one of the resilient mounting jaws completely removed from the invention for clarity.

FIG. 12 is a cross-sectional view taken along lines 12—12 of FIG. 6.

BEST MODE FOR CARRYING OUT THE INVENTION

Figure 1:
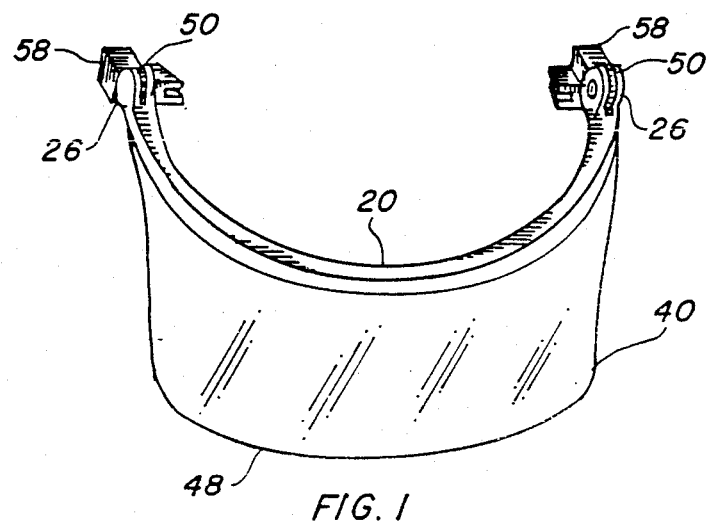
FIG. 1 is a partial isometric view of the preferred embodiment with a flat lens bottom edge.
Figures 2, 3:
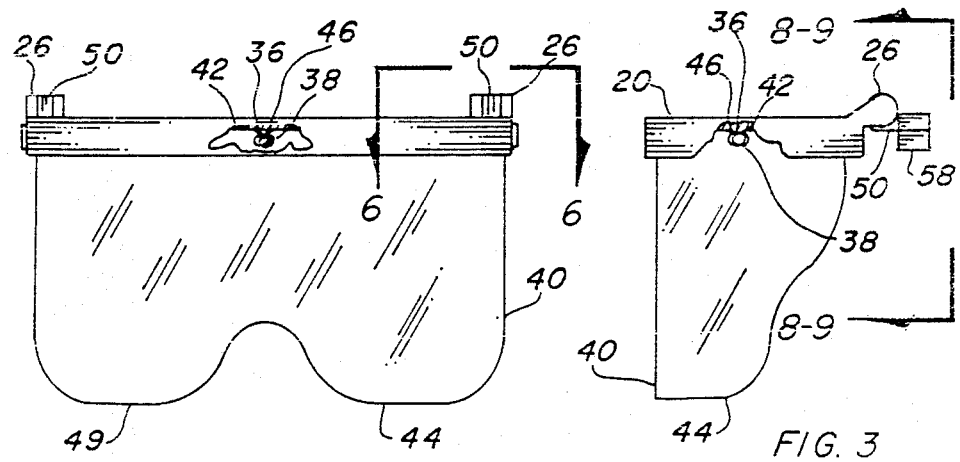
FIG. 2 is a front view of the preferred embodiment with the lens having an upwardly sloping radial shape in the center of the bottom edge.
FIG. 3 is a side view of the preferred embodiment as in FIG. 2.

The best mode for carrying out the invention is presented in the terms of a preferred embodiment, shown in FIGS. 1-12 with two separate lens configurations illustrated in FIGS. 1-3 with the invention primarily designed for use as a light reducing visor attached to a hat having an extended bill on the front. Referring now in detail to the drawings, the invention, as illustrated in FIG. 1-12, consists of a lens holder 20 in basically an angular cross-sectional configuration, best depicted in FIG. 12, in generally an inverted "L" shape, about the same size and contour as the bill 22 on a cap 24. The holder 20 has a bifurcated channel like socket 26, extending therethrough shown best in FIGS. 7 and 8. Each side of the channel 26 contains a bore 28 extending completely through the inside leg of the forked socket 26 and partially through the outside leg in parallel alignment. The angular configuration of holder 20 consists of a flat horizontal leg 30 and a pair of downwardly depending legs 32 and 34, FIG. 12, illustrating the cross-section. The outside downwardly depending leg 32 is slightly longer than the inside leg 34, with the pair creating a groove in between. The inside leg 34 contains a plurality of holes 36 in spaced relationship at a midpoint in the depending surface.

A plurality of round lens mounting sleeves 38 are pressed into the holes 36 in the leg 34 with a tight sliding fit. The sleeve 38 bridges the groove between the legs 32 and 34 with the end of the sleeve 38 touching the outside leg 32. This arrangement provides a series of sleeves 38 within the groove of the holder 20 in spaced relationship preferably five (5), however, any number over three (3) would be operably sufficient.

A resilient lens 40, having transparent properties, is utilized attached to the holder 20. This lens 40 has a flat depending top edge 42 and a contoured bottom edge 44 in two embodiments. Along the top edge 42 a plurality of keyhole shaped slots 46 are located through the material, best illustrated in FIG. 7. These slots 46 have a radial end and a narrower approach from the top edge 42. The radial end is the same size as the sleeves 38 allowing a nesting fit therebetween. The lens 40 is removably secured to the holder 20 by inserting it into the slot created between the legs 32 and 34. As the lens 40 is resilient, deformation occurs around the narrow portion of the slot 46 allowing it to spring around the sleeves 38 snapping into place snugly when forced thereupon. This attachment means allows the lens 40 to be easily removed and replaced or a substitute lens mounted in its place.

The preferred embodiment, shown in FIG. 1, has a straight contour 48 on the bottom edge 44 parallel with the lens holder 20. Another embodiment of the lens 40, shown in FIGS. 2 and 3, incorporates the bottom edge 44 formed with an upwardly sloping radial shaped contour 49 in the center providing a large surface to protect the face while allowing sufficient clearance for the wearers nose. In either embodiment, the translucent lens 40 may be color tinted at various densities to restrict the lights penetration protecting the wearers eyes from glare and certain undesirable light wave lengths. The lens 40 may be made of any relatively thin resilient thermoplastic material, such as cast acrylic methyl methacrylate, polyvinylidene fluorite, cellulose acetate, polyethylene, with polycarbonate being preferred.

The attachment of the holder 20 to a visored cap 24 utilizes a pair of cylindrically shaped swivel links 50, illustrated separated from the assembly in FIG. 10. The swivel link 50 is flat on one surface and cylindrical on the other with a rod shaped portion extending on one end. A cavity 52 is contained within the link 50 in the centermost part of the cylindrical portion and has a slit continuing from the cavity 52 to the outside surface. The rod portion contains a peripheral groove 54 near the end extending at right angles to the cavity 52. The slit from the cavity 52 is normally positioned on the bottom edge. The link is positioned within the forks of the socket 26 and frictionally constrained within this area with the bores 28 aligned making the link 50 a connecting member that rotates vertically within the confines of the socket 26.

A pair of hinge pins 56, best depicted in FIGS. 6 and 7, are pressed into the bores 28 of the sockets 26 and through the cavities 52 of the link 50 creating a rotatable joint. Each hinge pin 56 is tightly engaged by the bore 28 and movably contiguous with the cavity 52, thereby allowing the joint to move freely with a slight amount of tension, allowing the assembly to retain its location when moved upward out of the way of the bill on the cap 24. The hinge pin 56 is flush with the inside surface of the interior fork of the socket 26, so as to be unobstructive to the hat.

Two resilient mounting jaws 58 complete the attaching apparatus and consist of a structure with a round chamber 60 horizontal to the top and a hollow 62 at right angles thereto. Further, a pair of parallel jaw fingers 64 are disposed beneath the chamber 60. These fingers have a thinned portion near the innermost area allowing them to be sprung apart near the base creating a spring effect. A plurality of opposed teeth 66 are located on the inside surface to increase the gripping capabilities of the fingers upon the bill of a cap, allowing a varied range of thicknesses to be accommodated by the invention. The jaws 58 are attached to the link 50 with the rod portion rotatably penetrating the chamber 60 locked in place by a link locking swivel pin 68. One end of the link pin 68 is rotatably contiguous with the peripheral groove 54 in the rod of the link 50 and the other is flush with the outside surface. The hollow 62 is slightly smaller or equal to the diameter of the link pin 68, causing a press fit holding the pin in place. FIG. 11 illustrates this jaw 58 completely removed from the assembly in a horizontal position. The link pin 68 in the groove 54 provides the attachment between the link 50 and the jaw 58 while still allowing rotation.

Figures 4, 5:
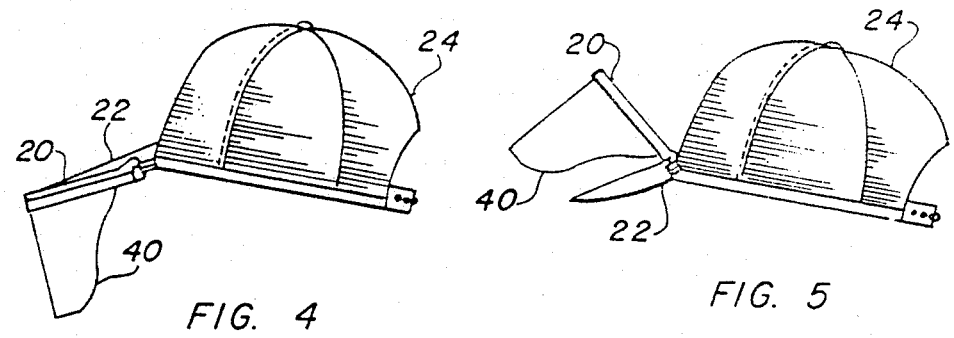
FIG. 4 is a side view of the preferred embodiment attached to the bill of a cap.
FIG. 5 is a side view of the preferred embodiment attached to the bill of a cap with the visor rotated upward away from the users face.

When the device is assembled and attached to a billed cap 24 with the jaws 58 resiliently grasping the bill, as shown in FIGS. 4 and 5, the lens 40 is positioned at right angles allowing the wearers face to be covered and protected. When this function is no longer wanted, the lens 40 within the holder 20 is rotated upwardly, as depicted in FIG. 5, and maintains its position by friction of the rotating elements. This rotation is controlled vertically by the link 50 within the socket 26 and axially with the rod portion of the link 50 rotating within the chamber 60 of the jaw 58. It can be clearly seen that this arcuate movement is possible with this composite of elements regardless of the angle of the bill of the cap 24 to which the device is attached.

All of the elements thus described, except the lens 40, are fabricated of a thermoplastic material molded by a method of injection well known in the art.

While the invention has been described in complete detail and pictorially shown in the accompanying drawings, it is not to be limited to such details, since many changes and modifications may be in the invention without departing from the spirit and the scope thereof. Hence, it is described to cover any and all modifications and forms which may come within the language and scope of the appended claims.

We claim:

1. An improved detachable visor of the type having a face shield privotally mountable on the bill of a cap wherein the improvement comprises:
   (a) a lens holder having an inverted "L" shape extending between terminating ends, each terminating end having a bifurcated channel like socket with portions defining a pair of parallel bores, said holder having a pair of downwardly depending parallel legs, one on the outside and the other on the inside, defining a groove therebetween, the inside leg having a plurality of holes through the leg in spaced relationship, the holder having a width between the terminating ends to correspond with the breadth of a bill on a cap;
   (b) a plurality of round lens mounting sleeves each embracingly grasped within a said hole in said inside leg of the holder on one end and contiguous with said outside leg of the holder on the other providing a bridge therebetween for attachment purposes within the groove of said lens holder;
   (c) a resilient lens with the properties of transparency having a flat depending top edge and a contoured bottom edge, the top further containing a plurality of keyhole shaped slots near the uppermost portion with the narrowest point smaller than said lens mounting sleeves and the largest radial end of the slot the same size, the lens is removably secured to said holder within said groove, the resiliency of the lens allowing deformation to occur around the slots when forced upon said sleeves providing securement thereupon;
   (d) a pair of cylindrically shaped swivel links, each link having a cavity with a slit continuing to the outside surface on one end, and a rod portion having a peripheral groove therein extending at right angles to the cavity on the other end, each link frictionally constrained within said bifurcated socket, the bores aligned with the cavity defining a connecting member with rotational capabilities in opposed directions;
   (e) a pair of hinge pins, each pin pressingly engaging the bores in said bifurcated socket and rotatably contiguous with said link cavity flush with the outside surface providing an arcuate union;
   (f) a pair of resilient mounting jaws, each jaw having a round chamber with a hollow at right angles thereto and a pair of parallel jaw fingers, rotatably attached to a said swivel link, the rod portion slideably embracing the chamber providing a jaw that is laterally and longitudinally rotatable with said lens holder, and the jaw fingers springingly grasping the edges of a bill on a cap for attachment thereunto; and,
   (g) a pair of link locking swivel pins, each said link pin engaging one of the said hollows and rotatably contiguous with the peripheral groove in said swivel link restraining the jaw and link together for attaching the visor to the bill of a cap on each side in such a manner as to provide adjustment throughout the full arcuate range of travel.

2. The invention as recited in claim 1 wherein said lens further comprises a tinted color for decreasing the light penetrating therethrough and said contoured bottom edge having a flat edge parallel to said lens holder.

3. The invention as recited in claim 1 wherein said lens further comprises a tinted color for decreasing the light penetrating therethrough and said contoured bottom edge having an upwardly sloping radial shape in the center for providing greater surface area while allowing a recess for the wearers nose.

4. The invention as recited in claim 1 wherein said mounting jaws further comprise a plurality of opposed teeth on the inside surface of said jaw fingers for increasing the gripping potential upon the bill of a cap within an extended range of thickness.

* * * * *